(12) United States Patent
Perkins et al.

(10) Patent No.: US 10,058,264 B2
(45) Date of Patent: Aug. 28, 2018

(54) METHOD AND APPARATUS FOR A UNIVERSAL SENSOR

(71) Applicant: Noraxon U.S.A., Inc., Scottsdale, AZ (US)

(72) Inventors: Brent R Perkins, Scottsdale, AZ (US); David K Byman, Cave Creek, AZ (US)

(73) Assignee: Noraxton U.S.A., Inc., Scottsdale, AZ (US)

( * ) Notice: Subject to any disclaimer, the term of this patent is extended or adjusted under 35 U.S.C. 154(b) by 0 days.

(21) Appl. No.: 15/454,580

(22) Filed: Mar. 9, 2017

(65) Prior Publication Data

US 2018/0132748 A1    May 17, 2018

Related U.S. Application Data

(60) Provisional application No. 62/421,016, filed on Nov. 11, 2016.

(51) Int. Cl.

| | |
|---|---|
| *A61B 5/0488* | (2006.01) |
| *A61B 5/0402* | (2006.01) |
| *A61B 5/08* | (2006.01) |
| *G01C 19/5776* | (2012.01) |
| *A61N 1/08* | (2006.01) |
| *A61B 5/00* | (2006.01) |
| *A61B 5/11* | (2006.01) |
| *A61B 5/22* | (2006.01) |

(52) U.S. Cl.
CPC .............. *A61B 5/0488* (2013.01); *A61B 5/00* (2013.01); *A61B 5/0402* (2013.01); *A61B 5/08* (2013.01); *A61N 1/08* (2013.01); *G01C 19/5776* (2013.01); *A61B 5/1107* (2013.01); *A61B 5/22* (2013.01); *A61B 5/222* (2013.01); *A61B 5/224* (2013.01); *A61B 5/227* (2013.01); *A61B 5/4519* (2013.01)

(58) Field of Classification Search
CPC ....... A61B 5/08; A61B 5/0488; A61B 5/0402; A61B 5/22; A61B 5/222; A61B 5/224; A61B 5/227; A61B 5/1107; A61B 5/4519; A61B 5/00; G01C 19/5776; A61N 1/08

See application file for complete search history.

(56) References Cited

U.S. PATENT DOCUMENTS

| | | | |
|---|---|---|---|
| 4,407,295 A | | 10/1983 | Steuer et al. |
| 5,331,851 A | * | 7/1994 | Parviainen ........... A61B 5/0488 |
| | | | 482/133 |

(Continued)

*Primary Examiner* — Rene Towa
(74) *Attorney, Agent, or Firm* — Michael T. Wallace

(57) ABSTRACT

A universal sensor pod provides a native sensing function during a first mode of operation and a secondary sensing function during a second mode of operation. The universal sensor pod may transition from the native sensing function to the secondary sensing function upon detecting that a sensor capable of the secondary sensing function is connected to the universal sensor pod via a smart connector. The universal sensor pod may continue one or more native sensing functions along with the secondary sensing function upon detecting that a sensor capable of the secondary sensing function is connected to the universal sensor pod via a smart connector. A code embedded within the smart connector is transmitted to a processor contained within the universal sensor pod and in response, the processor executes a firmware application that is tailored to the secondary sensing function code in response to receiving the code.

7 Claims, 12 Drawing Sheets

(56) References Cited

U.S. PATENT DOCUMENTS

| | | | |
|---|---|---|---|
| 5,804,971 A * | 9/1998 | Cumming | G01N 27/286 |
| | | | 204/406 |
| 5,813,404 A * | 9/1998 | Devlin | A61B 5/0416 |
| | | | 600/372 |
| 6,083,156 A * | 7/2000 | Lisiecki | A61B 5/02055 |
| | | | 600/301 |
| 6,712,762 B1 * | 3/2004 | Lichter | A61B 5/0205 |
| | | | 128/920 |
| 6,790,178 B1 * | 9/2004 | Mault | A61B 5/0011 |
| | | | 128/903 |
| 8,149,102 B1 | 4/2012 | Miller et al. | |
| 9,084,550 B1 * | 7/2015 | Bartol | A61B 5/0488 |
| 2003/0109905 A1 * | 6/2003 | Mok | A61B 5/0002 |
| | | | 607/60 |
| 2007/0042866 A1 * | 2/2007 | Skilken | A63B 21/00 |
| | | | 482/8 |
| 2007/0135264 A1 * | 6/2007 | Rosenberg | A63B 24/0062 |
| | | | 482/8 |
| 2010/0113898 A1 * | 5/2010 | Kim | A61B 5/0261 |
| | | | 600/310 |
| 2011/0201382 A1 | 8/2011 | Hsiao | |
| 2013/0144280 A1 | 6/2013 | Eckhouse et al. | |
| 2014/0275898 A1 | 9/2014 | Taub et al. | |
| 2016/0058301 A1 * | 3/2016 | Shusterman | A61B 5/0205 |
| | | | 600/301 |
| 2016/0124498 A1 * | 5/2016 | Chung | G01C 25/00 |
| | | | 345/156 |
| 2016/0242646 A1 | 8/2016 | Obma | |

\* cited by examiner

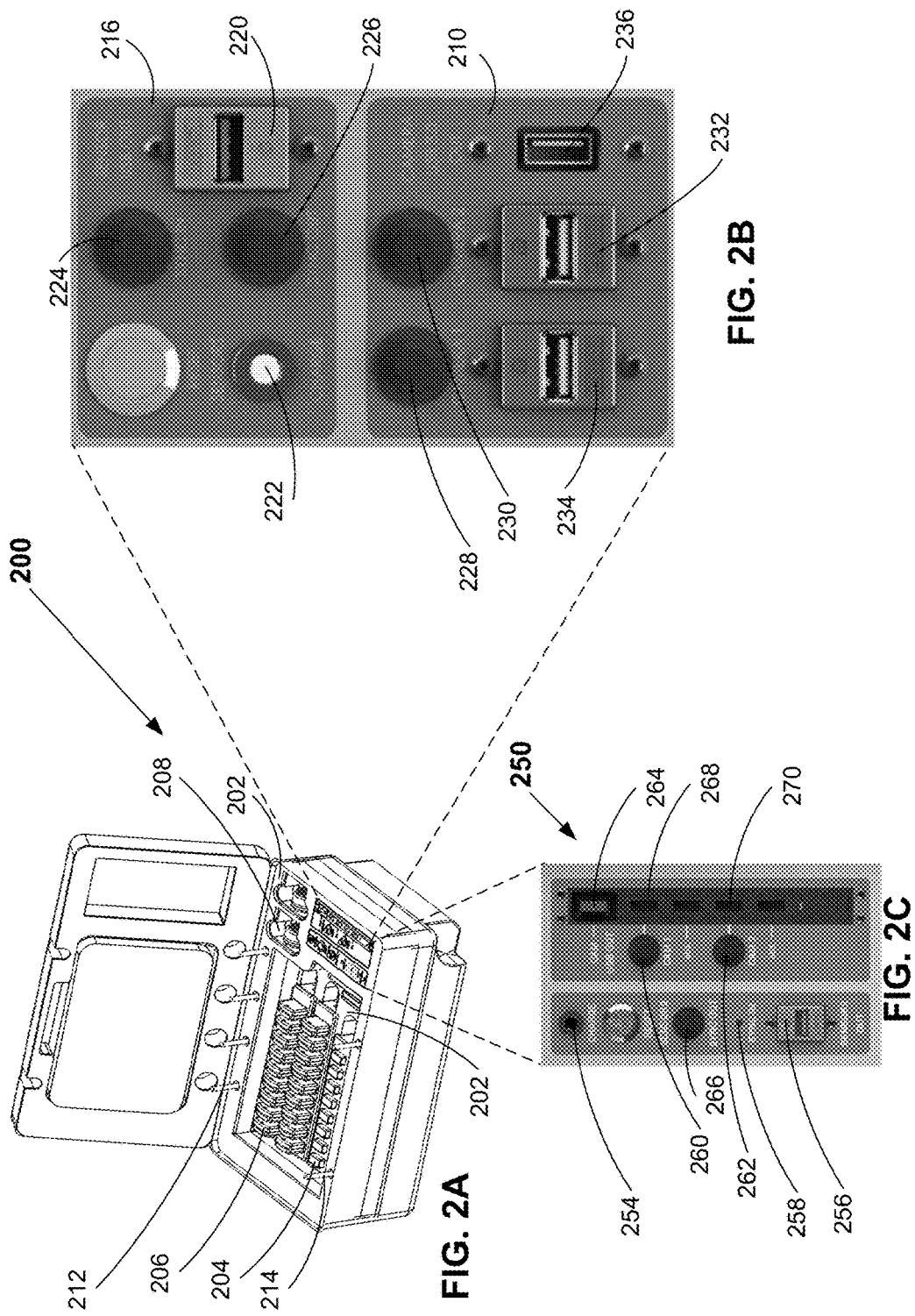

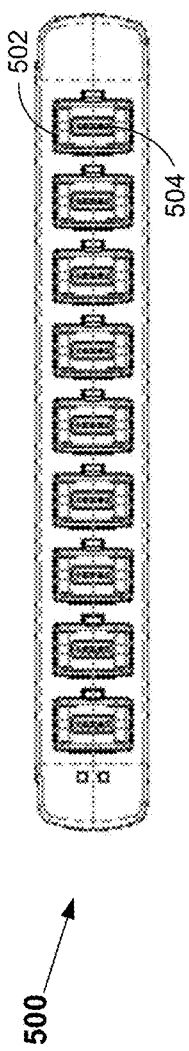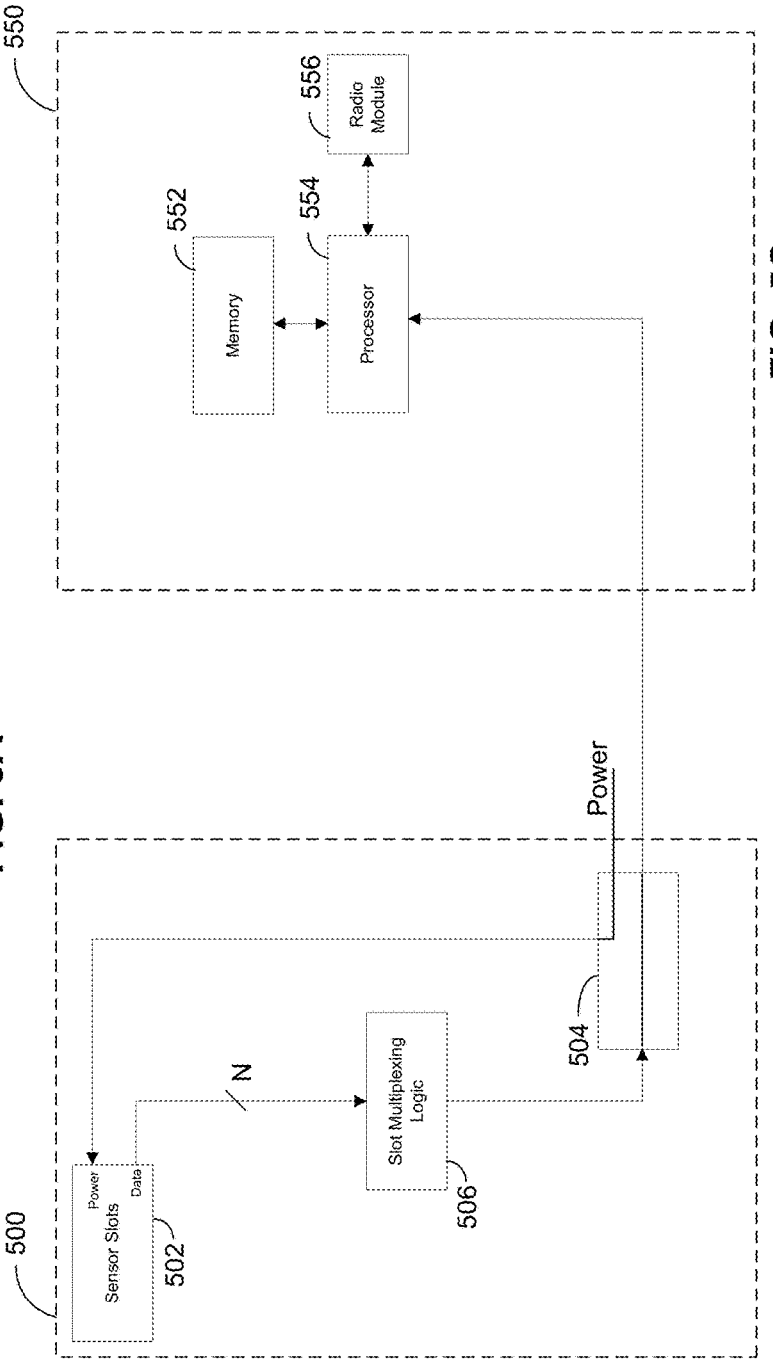

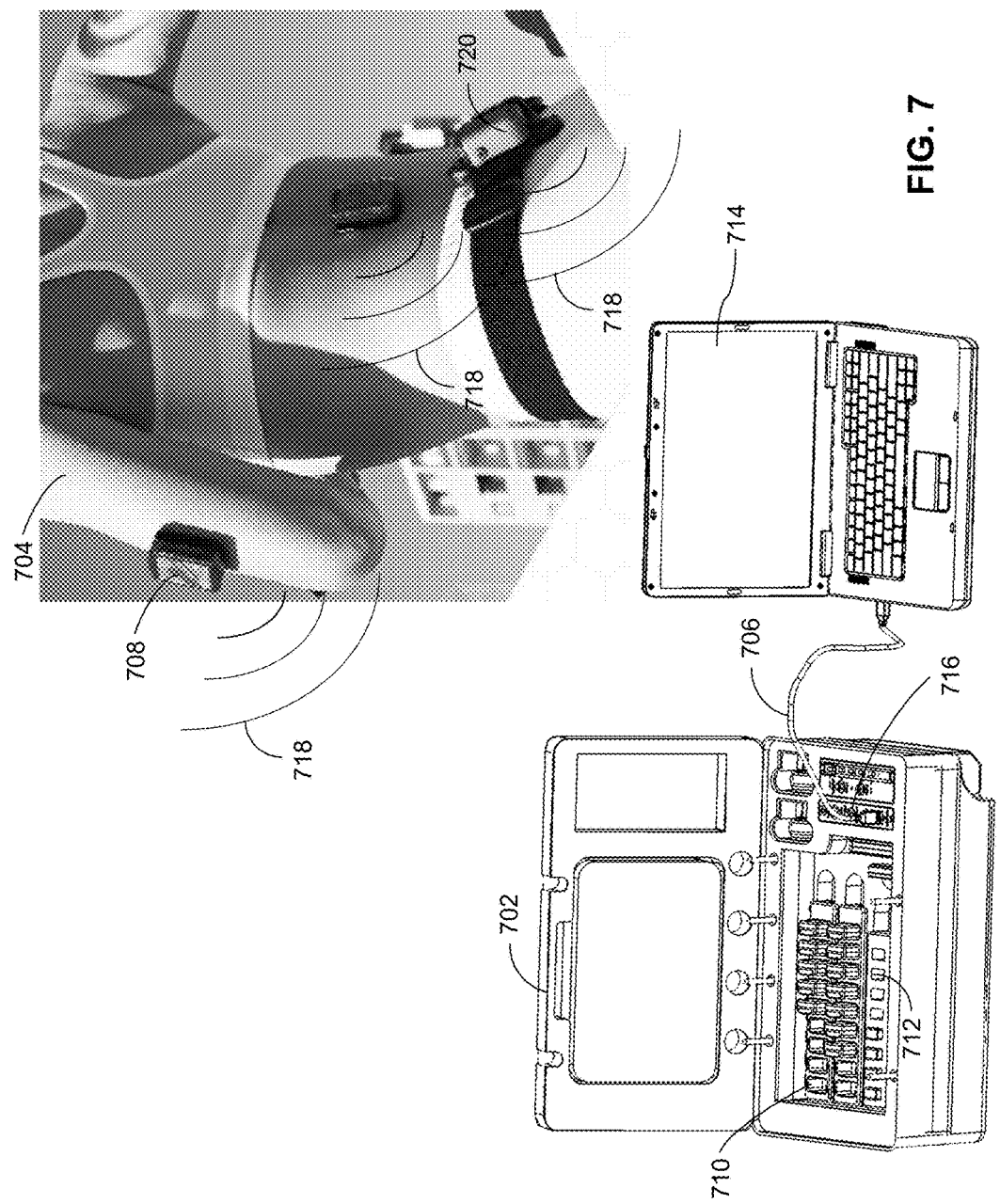

METHOD AND APPARATUS FOR A UNIVERSAL SENSOR

FIELD OF THE INVENTION

The present invention generally relates to universal sensors, and more particularly to automatically adaptive universal sensors.

BACKGROUND

Multiple disciplines in operation today may benefit from kinematic analysis adapted to capture movements and postures of the human body. Realistic animations for movies and computer games, for example, utilize kinematic analysis systems to more accurately capture movements of a human actor that may then be mapped onto an avatar hosted by the movie and/or computer game environment. In virtually all sports disciplines, kinematic analysis systems may be used to analyze and improve the performance of athletes by helping to analyze, for example, the athlete's vertical jump technique. In various medicinal disciplines, kinematic analysis systems may be used to evaluate and treat, for example, abnormal gait patterns.

In addition to kinematic analysis, conventional biomechanical assessment laboratories may also provide electromyographic (EMG) technologies, such as surface EMG (sEMG), to implement non-invasive procedures involving the detection, recording and interpretation of the electric activity of groups of muscles at rest and during activity. Still other assessment technologies employed by conventional biomechanical assessment laboratories may include kinetic assessment tools that may help to analyze causes of motion such as human strength and power.

The sensing of human movement employed by conventional biomechanical assessment laboratories may include the use of inertial and magnetic sensor modules to measure, for example, body segment orientation. Such inertial and magnetic sensors may measure the motion of each body segment to which they are attached and may include such measurements independently of other systems with respect to a particular reference system (e.g., an earth-fixed reference system). Such sensors may, for example, include any one or more of the following: 1) gyroscopes for measuring angular velocity; 2) accelerometers for measuring acceleration including gravity; and 3) magnetometers for measuring the earth's magnetic field. Knowledge as to any one or more of the EMG, kinetic and kinematic sets of sensor output data may be further combined with video data to augment analyses that may be performed by conventional biomechanical assessment laboratories.

Conventional sensor platforms, however, are tailored specifically to a particular sensing function. Each sensing function that may be required by a conventional biomechanical assessment laboratory, therefore, necessitates the use of specialized sensor platforms tailored to that specific sensor function even though many of the functions of the sensor platforms are duplicative (e.g., each sensor platform may include a battery, a processor and a memory). Accordingly, the use of customized sensor types may inefficiently utilize sensor functions due to their replication across all customized sensors.

Efforts continue, therefore, to develop more efficient sensor types.

SUMMARY

To overcome limitations in the prior art, and to overcome other limitations that will become apparent upon reading and understanding the present specification, various embodiments of the present invention disclose methods and apparatus for the mobilization of a biomechanical assessment laboratory. Other embodiments of the present invention disclose methods and apparatus for a standard sensor platform to assume multiple other sensor capabilities by utilizing a universal sensor configuration that includes a connector configured to detect a plurality of sensor types and associated processing to allow the universal sensor platform to assume the particularized operational capabilities of the detected sensor type. Other embodiments of the present invention disclose methods and apparatus that orient physical sensor devices (e.g., accelerometers) into particular geometric orientations that allow the sensor's native measurement capability (e.g., linear acceleration) to be manipulated into an alternate set of sensor information (e.g., angular velocity).

In accordance with one embodiment of the invention, a universal sensor comprises a sensor pod including a processor, a first memory coupled to the processor and configured with a plurality of executable applications and a second memory. The universal sensor further comprises a sensor assembly removably coupled to the sensor pod and configured to perform a first sensor function. The sensor assembly includes a first sensor configured to provide a first signal representative of a physical property associated with the first sensor function and a third memory configured to provide a code indicative of the first sensor function to the processor. The processor is configured to execute one of the executable applications in response to a value of the code, the executed application manipulating the first signal into a first result for storage in the second memory.

In accordance with another embodiment of the invention, a method of using a universal sensor comprises attaching a first sensor to a connector, the connector including a readable code indicative of a physical property associated with a first signal generated by the first sensor, programming a first memory of a sensor pod with a plurality of applications, attaching the connector to the sensor pod, reading the code from the sensor pod, generating the first sensor signal and executing one of the plurality of applications based on a value of the code to manipulate the first sensor signal into a first result stored within a second memory of the sensor pod.

In accordance with another embodiment of the invention, a method of operating a universal sensor pod comprises establishing a native sensing function of the universal sensor pod, coupling a sensor to the universal sensor pod, the sensor configured to implement a secondary sensor function, detecting the secondary sensor function in response to the coupling and changing the native sensing function to the secondary sensor function in response to the detecting.

BRIEF DESCRIPTION OF THE DRAWINGS

Various aspects and advantages of the invention will become apparent upon review of the following detailed description and upon reference to the drawings in which:

FIG. 2A illustrates the portable laboratory of FIG. 1 that is configured for internal access;

FIGS. 2B-2C illustrate alternate configurations of patch panel data input and output of the portable laboratory of FIG. 2A;

FIGS. 5A and 5B illustrate a docking station in accordance with one embodiment of the present invention;

FIG. 5C illustrates a block diagram of a sensor data receiver in accordance with one embodiment of the present invention;

FIG. 7 illustrates an environmental test conducted by a portable laboratory in accordance with one embodiment of the present invention;

DETAILED DESCRIPTION

Generally, the various embodiments of the present invention are applied to a portable biomechanical assessment laboratory (PBAL) integrating kinetic, kinematic and electromyographic (EMG) technologies into a single, portable system to maintain integrity of research and data collection fidelity irrespective of the environment within which the PBAL operates. Furthermore, the PBAL is ruggedized to substantially absorb shock and vibration during transit, while at the same time protecting the individual components from environmental contamination that may be caused by precipitation or other environmental contaminants.

The PBAL may include universal sensor pods that may incorporate battery, processor and wireless communication components, which combine to implement baseline functionality along with native EMG measurement and Inertial Measurement Unit (IMU) capability. Specific sensor modules may interface with the universal sensor pods to augment the baseline functionality of the universal sensor pod to include various other sensing capabilities, such as acceleration, pressure, and force measurement capability. Dynamometers, biosensors (e.g., respiration and electrocardiogram (ECG)), goniometers, generic analog sensors (e.g., +/−10V analog sensors) and generic digital sensors may further be accommodated by the universal sensor pod.

Integrated video/lighting components may further be incorporated into the PBAL, which not only provide the necessary illumination to highlight the subject of the biomechanical assessment (e.g., highlight reflective markers that are attached to the subject of the biomechanical assessment), but also the video capture capability that may be needed to be combined with the kinetic, kinematic, EMG and other sensing technologies integrated within the PBAL. A patch panel may also be provided within the PBAL such that each of the multiple biomechanical assessment technologies may be appropriately interconnected and synchronized with a biomechanical assessment software application that may be executing on a computing station in proximity to the PBAL.

Figure 1:
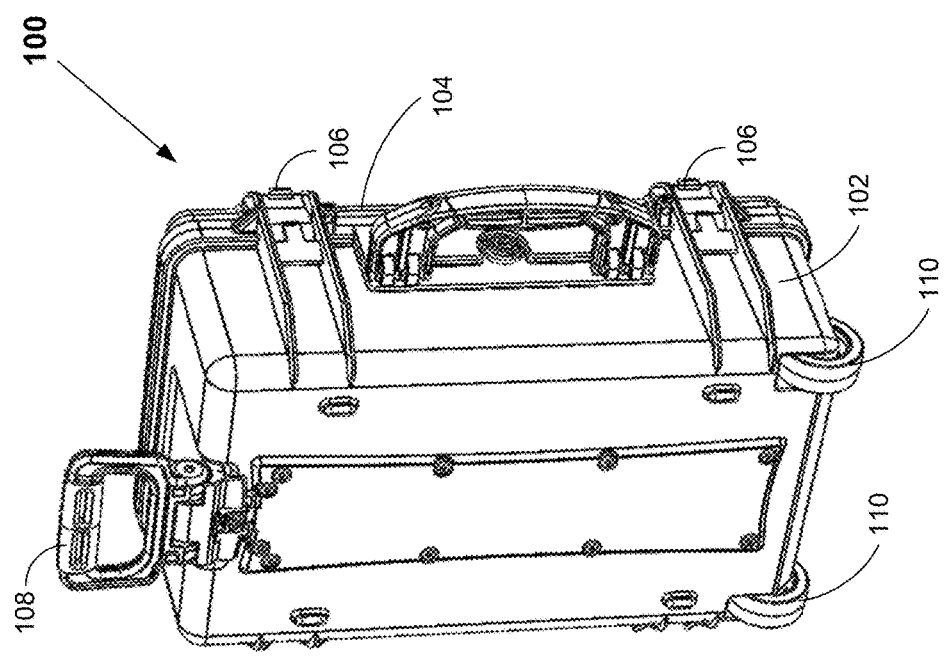
FIG. 1 illustrates a portable laboratory in accordance with one embodiment of the present invention.

Turning to FIG. 1, PBAL 100 is exemplified in its fully mobilized form. As illustrated, the contents of PBAL 100 may be completely enclosed by outer shell 102, which may be comprised of any shock-resistant material (e.g., polycarbonate) and that may be resistant to environmental contaminants (e.g., dirt and moisture) thereby maintaining the integrity of the biomechanical assessment technologies (not shown) contained within an interior of PBAL 100. For example, PBAL 100 may employ hatch mechanism 104, which may include sealing components (e.g., water-proof gaskets not shown), such that once hatch mechanism 104 is secured against outer shell 102 via, for example, locking mechanisms 106, water-proof gaskets (not shown) may be compressed between outer shell 102 and hatch mechanism 104 to seal and substantially protect the biomechanical assessment technologies (not shown) housed within an interior of PBAL 100 from environmental contaminants. In alternate embodiments, sealing components of PBAL 100 may not employ gaskets, but may instead employ other mechanisms (e.g., interlocking channels) to seal and substantially protect an interior of the biomechanical assessment technologies from environmental contaminants.

As exemplified in FIG. 1, PBAL 100 may further include a handle (e.g., telescoping handle 108) and/or mobilization devices (e.g., casters 110) to facilitate transportation of PBAL 100 to virtually any environment within which it is to be used. Virtually any venue within which biomechanical assessment data may be required to be collected, synchronized, integrated and analyzed may be facilitated by PBAL 100.

Figure 2D:
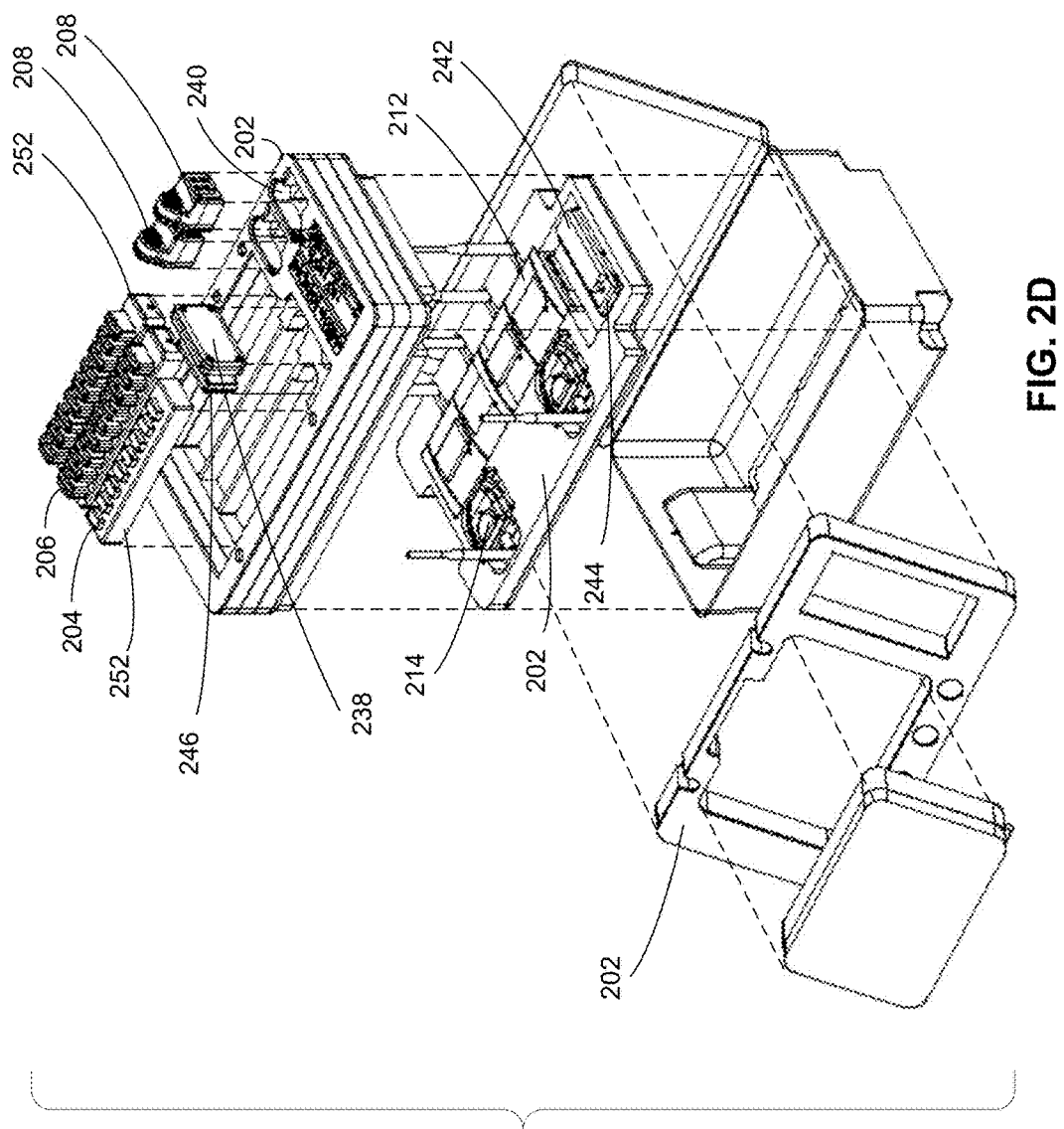
FIG. 2D illustrates an exploded view of the portable laboratory of FIG. 2A.

Turning to FIG. 2A (and the associated exploded view of FIG. 2D), PBAL 200 is exemplified in a configuration that may allow access to the biomechanical assessment technologies that may be housed within PBAL 200 along with supporting infrastructure (e.g., patch panels 210, 216 and docking stations 252). Any number of biomechanical assessment technologies may be housed within PBAL 200, which may include electromyography (EMG) sensors (e.g., EMG sensors 204), kinematic sensors (e.g., inertial measurement units (IMUs) 206), docking stations (e.g., EMG and IMU data interconnect and/or charging stations 252), video capture devices (e.g., cameras 208), wireless radio devices (e.g., receivers 212 and 214), networking devices (e.g., universal serial bus (USB) hub 242), a signal generator (e.g., synchronization signal generator 244), optical signal generator (e.g., synchronization light generator 246), miscellaneous devices (e.g., data logger 238) and data and power interconnect (e.g., patch panel 210 and 216) to name only a few. It should be noted that any data and power interconnect configuration may be implemented within PBAL 200, such as patch panel 250 as exemplified in FIG. 2C, which may be utilized in lieu of patch panels 210 and 216.

The biomechanical assessment technologies contained within PBAL 200 may be segmented, compartmented and interconnected to allow, among other things, shock and vibration isolation (e.g., via foam inserts 202), charging of the battery operated components contained within PBAL 200 (e.g., EMG sensors 204 and IMUs 206) via charging stations 252 and data input/output facilities required during operation (e.g., patch panels 210,216 or 250).

IMUs 206 may, for example, contain any one or more inertial measurement components, such as: 1) gyroscopes, which may be used to measure angular velocity; 2) accelerometers, which may be used to measure acceleration including gravity as well as to estimate angular velocity as discussed in more detail below in relation to FIG. 8; and 3) magnetometers for measuring the earth's magnetic field, which when combined with the accelerometer and gyroscopic capabilities, may form an attitude and heading reference system (AHRS). Other measurement components (e.g., temperature sensors) may also be included within IMUs 206 to, for example, provide calibration data that may be necessary to calibrate the inertial measurements taken by IMUs 206 over a particular temperature range. It is further noted that IMUs 206 may provide internal computational capability (e.g., as provided by an internal processor and associated firmware-based algorithm executed by the internal processor) on each measurement, or groups of measurements, taken. Accordingly, for example, the angular velocity measurements taken by the gyroscope of IMU 206 may be integrated once by the internal processor to obtain orientation information. Similarly, acceleration measurements taken by the accelerometer of IMU 206 may be integrated once to obtain velocity information and integrated a second time to obtain position information.

IMUs 206 may further include multiple sets (e.g., two sets) of accelerometers and gyroscopes for optimized performance across multiple axes (e.g., three axes) of movement. For example, two sets of accelerometers may be utilized within IMUs 206, whereby a first set of accelerometers may be optimized to measure an acceleration range between, for example, 0 and 2 times the earth's gravitational force (0-2 Gs) along each of the X, Y and Z axes, while a second set of accelerometers may be optimized to measure an acceleration range between, for example, 0-16 Gs along each of the X, Y and Z axes. A software algorithm executing on the processor within each IMU 206 may then choose one set of data from the available two sets of acceleration data depending upon the set of data that is the most accurate based on the G-load being experienced by IMU 206 at the time of measurement. For example, a first set of acceleration data (e.g., acceleration data taken during a 0G to 1.5G acceleration event) may be selected for use from the accelerometer that is optimized for use in that acceleration range and a second set of acceleration data (e.g., acceleration data taken during a 1.5G to 16G acceleration event) may be selected for use from the accelerometer that is optimized for use in that acceleration range.

Similarly, for example, two sets of gyroscopes may be utilized within IMUs 206 during operation—a first set of gyroscopes optimized for use at a first angular velocity (e.g., 0 to 600 degrees per second) and a second set of gyroscopes optimized for use at a second angular velocity (e.g., 0 to 2000 degrees per second). In an alternate embodiment, as discussed in more detail below in relation to FIG. 8, multiple accelerometers (e.g., 3 accelerometers) may be geometrically configured (e.g., into an "L" shape on a single plane of a printed circuit board) to measure much higher gyroscopic rates (e.g., up to 8000 degrees per second). It should be noted generally that acceleration data may be utilized to determine, for example, substantially static attitude parameters (e.g., pitch and roll) while gyroscopic data may be utilized to more accurately determine, for example, substantially dynamic parameters (e.g., the angular velocity and acceleration of movement of a particular body segment).

Each analog output of each accelerometer, gyroscope and magnetometer of each IMU 206 may be sampled internally (e.g., via an analog to digital (A/D) converter) to provide multiple sets of digital information. Two or more sets of digital information may then be fused (e.g., by a Kalman filter algorithm) within each IMU 206 to generate the orientation information associated with each IMU 206. In one embodiment, a four-dimensional orientation result (e.g., a quaternion) may be generated by each IMU 206, where quaternions may be transmitted (e.g., wirelessly transmitted) at a rate between about 100 and 1000 Hz (e.g., approximately between about 100 and 400 Hz) to an associated receiver within PBAL 200 (e.g., receiver 212) via any one of a number of communication protocols (e.g., any protocol that may utilize a direct sequence spread spectrum (DSSS) modulation format). In alternate embodiments, raw samples from each accelerometer, gyroscope and magnetometer may also be transmitted by each IMU 206 to receiver 212.

It should be noted that each IMU 206 must first be removed from PBAL 200 and placed onto a particular body segment of a particular subject under test before any meaningful orientation information may be obtained for that body segment as discussed in more detail below with respect to FIG. 7. As an example, sixteen IMUs 206 may be applied to sixteen different body segments before the orientation information from each IMU 206 may be utilized to form a full-body model (e.g., a full-body model as may be generated by a biomechanical analysis software application executing on a computing platform (not shown) connected to PBAL 200).

Each IMU 206 may facilitate wireless communications using a particular modulation format (e.g., direct sequence spread spectrum format) that may be used to communicate orientation information to motion data receivers (e.g., wireless communications to IMU receiver 212). Alternatively, each IMU 206 may instead wirelessly communicate to data logger 238, which may also be attached to the subject under test, such that the wireless communication distance between each IMU 206 and data logger 238 may remain substantially fixed between about less than one foot and several feet.

In one embodiment, a single motion data receiver 212 may communicate with multiple IMUs (e.g., up to 9 IMUs 206). Accordingly, multiple motion data receivers 212 may be utilized depending upon the number of IMUs that are required (e.g., two motion data receivers 212 are required to receive motion data from the 16 IMUs required for a full-body model). In this way, for example, PBAL 200 may be said to be a modular system where, for example, added capability may be achieved by simply cascading multiple motion data receivers 212 to achieve an extended bandwidth of operation.

EMG sensors 204 may further be included within PBAL 200. Each EMG sensor 204 may, for example, also include a wireless interface to facilitate wireless communications (e.g., wireless communications to EMG receiver 214 and/or wireless communications to data logger 238). Both IMUs 206 and EMGs 204 may, for example, be interconnected by a power charging bus (e.g., charging station 252) as discussed in more detail below in relation to FIGS. 5A and 5B, whereby once IMUs 206 and EMGs 204 are placed into charging station 252 of PBAL 200 as shown, IMUs 206 and EMGs 204 may receive power (e.g., at 5 VDC) that may be supplied externally (e.g., via connector 222 of patch panel 216 or connector 254 of patch panel 250) to charge the internal batteries of IMUs 206 and EMGs 204.

Patch panel 210, 216 or 250 may be interconnected via network devices (e.g., USB hub 242) so that sensor data received by receivers 212 and 214 may be submitted for upload by PBAL 200 via a master data upload port (e.g., USB port 220 or USB port 256). All data received by receivers 212 and 214 may be synchronized via a master synchronization signal provided to patch panel 216 or 250 (e.g., via connector 224 or connector 258) which may then be routed to receivers 212 and 214. A synchronization output signal (e.g., as may be provided by synchronization signal generator 244) may also be provided at patch panel 216 (e.g., via connector 226) or patch panel 250 (e.g., via connector 266), which may then be patched over to video capture synchronization connectors (e.g., 228 and 230 of patch panel 210 or connectors 260 and 262 of patch panel 250) so that video capture devices (e.g., cameras 208) may be synchronized to the data being collected by receivers 212 and 214.

In alternate embodiments, a visible signal (e.g., a flash of light as may be generated by synchronization light generator 246) may instead be detected by cameras 208 (e.g., received by a lens of cameras 208), which upon receipt, may also serve to synchronize cameras 208 to the data being collected by receivers 212 and 214. Video information collected by cameras 208 may be transferred to USB ports 232, 234 or USB ports 268, 270 which may then be collected by a network device (e.g., USB hub 242) and submitted for upload by PBAL 200 via a master video data upload port (e.g., USB port 236 or 264).

Figure 3B:
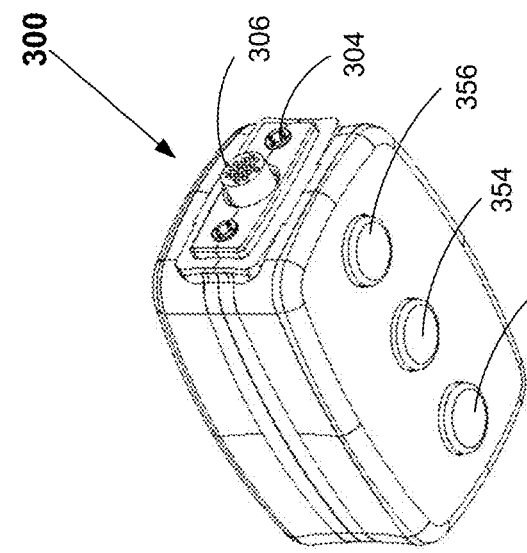
FIGS. 3A-3B illustrate a universal sensor pod in accordance with one embodiment of the present invention.
Figure 3A:
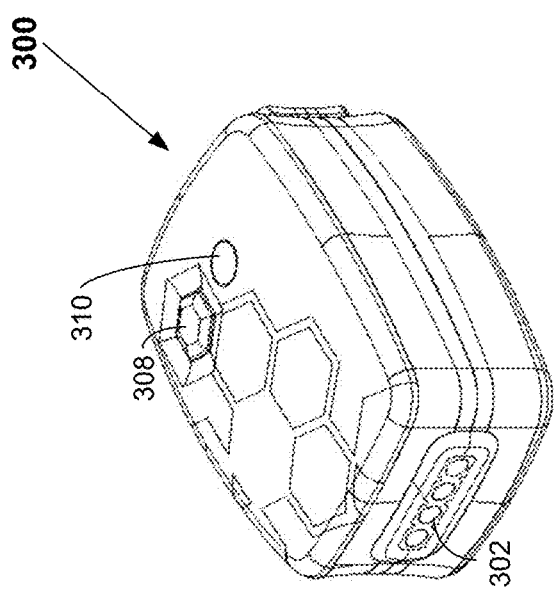
Figure 3C:
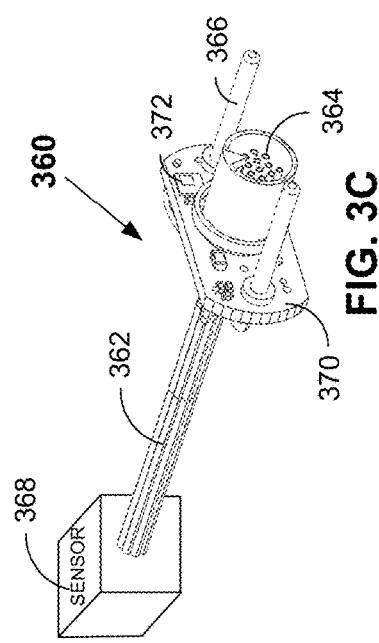
FIG. 3C illustrates a sensor and associated smart connector in accordance with one embodiment of the present invention.

In one embodiment, single-function IMUs 206 and EMGs 204 within PBAL 200 may be implemented using a universal sensor (e.g., universal sensor pod 300 and sensor assembly 360) as exemplified in FIGS. 3A-3C. As shown in FIG. 3A, universal sensor pod 300 may include connector 302, which may provide any number of electrodes (e.g., 4) that may be configured to receive a set of power signals (e.g., +5 VDC and a ground reference) as well as a set of data signals (e.g., a two-wire data interface) that may accommodate, for example, universal asynchronous receiver/transmitter (UART) communications as defined by the RS232 communication protocol among others.

As exemplified in FIG. 3B, universal sensor pod 300 may further include any number (e.g., 2) of EMG electrodes (e.g., EMG electrodes 352 and 356) such that once applied to a particular body segment of a subject under test, the electric potential generated by the associated muscle cells of the body segment may be sampled and prepared for transmission to an associated receiver. A third EMG electrode (e.g., EMG electrode 354) may, for example, be advantageous as a reference electrode, so as to provide a reference for common mode rejection to reduce noise and increase stability of the detected and sampled muscle activity.

Universal sensor pod 300 may, for example, provide the common functionality that may be associated with other sensors (e.g., IMUs 206 and EMGs 204), which as discussed above, may include a processor, a battery, a wireless interface and memory (e.g., on-board flash memory of the processor) that may be programmed (e.g., wirelessly programmed) with the software that is to be executed by the processor. Universal sensor pod 300 may further include a manual interface (e.g., button 308), which may be used, for example, to activate and deactivate universal sensor pod 300 and to provide data input to universal sensor pod 300. For example, each depression of button 308 may cycle through two or more operational modes of universal sensor pod 300. Universal serial pod 300 may, for example, further include a visible indication (e.g., illumination of light pipe 310) as to its operational state. For example, an LED (not shown) in proximity to light pipe 310 within sensor pod 300 may provide pulses of green light to indicate normal operation of universal serial pod 300 and may provide a constant red light indicative of abnormal operation.

The particular sensor function that may be performed by universal sensor pod 300 may be defined, for example, by sensor 368 of FIG. 3C once sensor 368 becomes mechanically and electrically engaged with connectors 304 and 306 of universal sensor pod 300. Sensor 368 may, for example, be interconnected to universal sensor pod 300 via a multi-pin interface (e.g., 16-pin connector 364, 16-pin connector 306 and multi-conductor cable 362). Sensor 368 may, for example, be further connected to universal sensor pod 300 via a multi-pin interface (e.g., 2-pin connector 366 and 2-pin connector 304), which may serve both a mechanical purpose (e.g., pins 366 may ensure a proper mechanical interface between connectors 306 and 364) while at the same time propagating a data signal (e.g., an EMG data signal) to internal electronics (e.g., an A/D converter not shown) within universal sensor pod 300.

Sensor assembly 360 may further include a printed circuit board (e.g., PCB 370) that may include a memory (e.g., EEPROM 372) which may, among other things, include a code that may identify the type of sensor function implemented by sensor 368. Sensor 368 may implement various sensor functions, such as acceleration measurements, pressure sensing, force sensing and may include various sensor types, such as a hand dynamometer, a finger pinch force sensor, a biosensor (e.g., respiration and ECG) and a goniometer to name only a few. In addition, virtually any analog sensor that may generate a known voltage output range (e.g., +/−10V) may also be utilized as sensor 368. Accordingly, a unique code that may be indicative of each available sensor 368 type may be programmed into EEPROM 372, which may then be detected by a processor (not shown) within universal sensor pod 300 to determine which sensor function may be performed by sensor assembly 360 once engaged with universal sensor pod 300.

Figure 4:
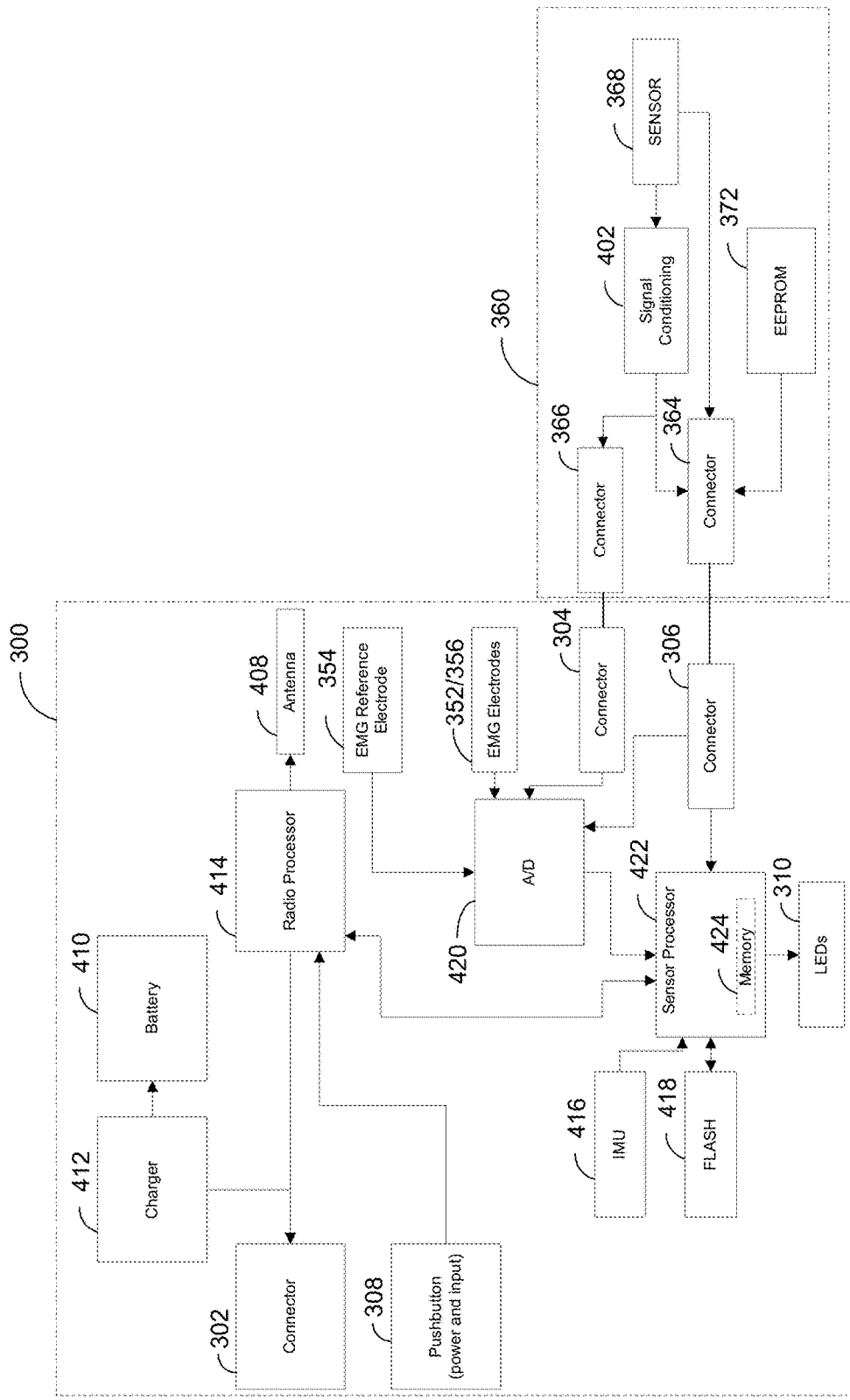
FIG. 4 illustrates a block diagram of the sensor and associated smart connector of FIG. 3C.

Turning to FIG. 4, a block diagram of universal sensor pod 300 and sensor assembly 360 are exemplified. As discussed above, engagement of connecters 364 and 306 may cause a code contained within EEPROM 372 to be read by sensor processor 422, which may identify the type of sensor 368 that may be connected to universal sensor pod 300. Signal conditioner 402 may, for example, provide signal conditioning functions (e.g., low-pass filtering, amplification and isolation) before the analog signal from sensor 368 is applied to A/D converter 420 for sampling. In alternate embodiments, sensor 368 may instead provide a digital output format, in which case signal conditioning 402 and A/D converter 420 may be bypassed and the digital information from sensor 368 may be directly provided to sensor processor 422.

As discussed above, connector 366 and 304 may interconnect to ensure a proper mechanical engagement between connectors 306 and 364. In addition, connectors 366 and 304 may further provide electrical interconnectivity between sensor assembly 360 and universal sensor pod 300. For example, sensor 368 may implement an EMG function whose associated data may be propagated to A/D 420 via connector pair 366/304 instead of, or in addition to, connector pair 364/306.

Sensor processor 422 may execute operational code (i.e., firmware) that may exist within memory (e.g., sensor processor 422 on-board memory 424), which may be dependent upon which type of sensor 368 is plugged into universal sensor pod 300. As an example, sensor 368 may be an accelerometer whose function is sensed by sensor processor 422 via a code retrieved from EEPROM 372. As a result, firmware resident within memory 424 may be executed by sensor processor 422 that is relative to the acceleration data generated by sensor 368. Accordingly, for example, after the acceleration data is sampled by A/D 420, it may be integrated once by sensor processor 422 in order to obtain velocity information and integrated a second time to obtain position information.

It should be noted, therefore, that firmware resident within memory 424 may be executed to collect, store and manipulate the physical properties that the sensor data represents. In one embodiment, for example, sensor 368 may produce multiple sets of linear acceleration data along three orthogonal axes and sensor processor 422 may execute firmware relevant only to sensor 368 to manipulate the conditioned and sampled linear acceleration data, thereby producing angular velocity estimates, as discussed below, for example, in relation to FIG. 8 and equations 1 through 35. Such angular velocity estimates may then be made available within flash memory 418 for future reference.

Alternately, or in addition, A/D 420 may sample EMG information being generated by EMG electrodes 352 and 356 as referenced to EMG reference electrode 354 before being processed by sensor processor 422 as may be defined by an EMG software processing module resident within on-board memory 424 of sensor processor 422. In other embodiments, universal sensor pod 300 may include internal IMU 416, which may include any one or more of an accelerometer, a gyroscope and/or a magnetometer whose data may be processed by sensor processor 422 in accordance with an IMU software processing module resident within on-board memory (e.g., flash memory 424 resident within sensor processor 422).

Sensor processor 422 may provide results of all executed sensor software processing modules to radio processor 414, which may then process the information for transmission to its associated receiver (e.g., receiver 212 and/or receive 214 of FIGS. 2A and 2D) via antenna 408. Radio processor 414 may utilize any data format to modulate a radio frequency carrier signal prior to transmission by antenna 408. Sensor processor 422 may further perform a data logger function, whereby all data transmitted to an associated receiver (e.g., receiver 212 and/or receive 214 of FIGS. 2A and 2D) may also be saved into flash memory 418 for future reference.

Connector 302 may, for example, include various charging pins (e.g., a +5 VDC charging pin and a ground reference pin) whereby a power signal supplied to universal sensor pod 300 may be processed (e.g., regulated from +5 VDC to +3.7 VDC) by charger 412 in order to be compatible with an internal power source (e.g., lithium battery 410). In alternate embodiments, connector 302 may include data pins to provide, for example, a wired data interface to any device that may be connected to universal sensor pod 300 via connector 302. As an example, the data logs contained within flash 418 may be transmitted (e.g., via hard-wired transmission via connector 302 and docking station 252) to an associated receiver (e.g., receiver 212 and/or receive 214 of FIGS. 2A and 2D) so that the associated receiver may compare the data wirelessly transmitted by radio processor 414 to data received via connector 302 so as to ensure the fidelity of data received wirelessly. If data gaps exist in the wirelessly received data (e.g., data gaps created by intermittent wireless communication), then the associated receiver may fill them with the data received via connector 302 from flash 418.

Turning to FIG. 5A, a plan view of docking station 500 is exemplified, which may provide docking functionality for any number of sensor technologies (e.g., IMUs 206 and EMGs 204 of FIG. 2 and universal sensor pod 300 of FIGS. 3A and 3B) that may be accommodated within a portable biomechanical assessment laboratory (e.g., as discussed above in relation to charging stations 252 of PBAL 200 of FIGS. 2A and 2D). It should be noted that slot 502 may be sized to accommodate any sensor technology and connector 504 may accommodate any number of conductors depending upon the functionality desired. For example, docking station 500 may provide charging capability only (e.g., as may be required by IMUs 206 and EMGs 204 of FIGS. 2A and 2D), thereby requiring a minimum number of conductors (e.g., 2 conductors). If, however, docking station 500 provides data capability (e.g., as may be required by universal serial pods 300 of FIG. 3), then more conductors may be required (e.g., 4 conductors total, 2 for power propagation and 2 for data propagation).

Turning to FIG. 5B, a block diagram of docking station 500 is exemplified, which may contain any number of sensor slots 502 (e.g., 9 as exemplified in FIG. 5A). In one embodiment, sensor slots 502 may only provide charging capability, in which case only power signals (e.g., +5 VDC and a reference as received from patch panel 216 or 250 of FIGS. 2B and 2C or USB power as may be received from laptop 714 via patch panel 716 of FIG. 7) may be routed through connector 504 to sensor slots 502.

In an alternate embodiment, data functionality may be provided, whereby a data path may exist between sensor slot 502, slot multiplexing logic 506 and connector 504, which as discussed above in relation to FIG. 4, may provide a data path whereby logged data (e.g., logged data contained within flash 418 of FIG. 4) may be transferred from a sensor that is plugged into sensor slot 502 (e.g., universal sensor pod 300) to a corresponding memory location of a receiver (e.g., memory 552 of receiver 550 of FIG. 5C). In such an instance, processor 554 of receiver 550 may compare wireless data previously received from the sensor via radio module 556 to the data logged by that same sensor. If any data is missing from the wireless data received from that sensor, as may be the case, for example, if the wireless transmission link failed at any time during transmission, then the logged data may be used to fill in data gaps within memory 552 that may be caused by such a transmission link failure.

Figure 6B:
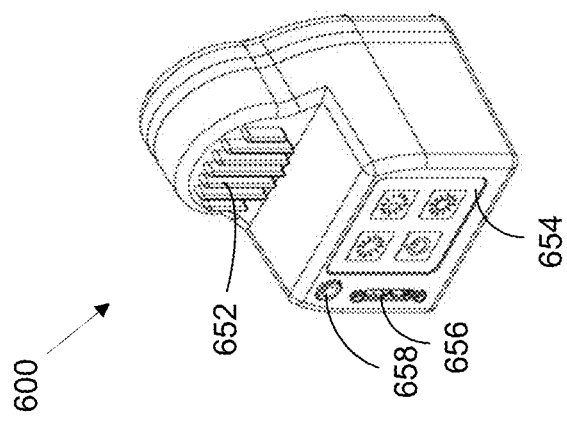
FIGS. 6A-6B illustrate a video capture device in accordance with one embodiment of the present invention.
Figure 6A:
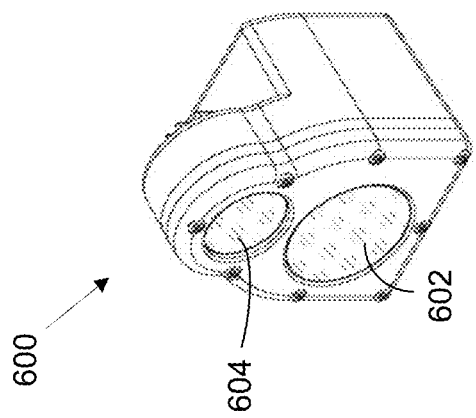

Turning to FIGS. 6A and 6B, front and back perspective views, respectively, of video capture device 600 are exemplified, whereby FIG. 6A exemplifies a front perspective view of video capture device 600 and FIG. 6B exemplifies a back perspective view of video capture device 600. It should be noted that one or more video capture devices 600 may, for example, be placed within a portable biomechanical assessment laboratory (e.g., cameras 208 of PBAL 200 of FIG. 2D) to be protected from shock and vibration (e.g., via foam insert 202 of PBAL 200 of FIG. 2D).

Video capture device 600 may, for example, include both an internal camera (e.g., an internal camera behind lens 602) and an internal lighting device (e.g., an internal LED behind lens 604) both of which may derive operational power from the power input as provided by USB interface 656. Manual control of the intensity of light generated by the internal LED may be accomplished via keypad 654, or remotely via USB interface 656. For example, keypad 654 may provide a limited number of intensity variations (e.g., high, medium, low and off), where each may be selected individually by depression of the respective icons of keypad 654.

Heat sink fins 652 may, for example, provide a heat conduction path, whereby heat generated by the LED may be conducted to heat sink fins 652. Convection may then be used to transfer the heat away from heat sink fins 652 and into the surrounding environment, thereby bringing the overall temperature of video capture device 600 within operational limits while video capture device 600 is in operation.

Video capture device 600 may be used during operation of a portable biomechanical assessment laboratory (e.g., PBAL 200 of FIGS. 2A and 2D), whereby high resolution video data may be captured at a variable frame rate (e.g., between about 30 and 500 frames per second) at variable frame resolutions (e.g., between about 720×280 pixels per frame to about 1600×1200 pixels per frame).

Video capture may be synchronized to the other data collection operations of a portable biomechanical assessment laboratory (e.g., IMUs 206 and EMGs 204 of PBAL 200 of FIGS. 2A and 2D) via a synchronization signal that may be received at synchronization port 658. Video data, for example, may be used to augment the validity of kinematic data when the video data is synchronized to the kinematic data. As an example, deviations in the kinematic data (e.g., unusually fast movements of the subject under test) may be compared to the frame-by-frame synchronized video data to determine whether the kinematic data represents an anomaly during that time period, or whether the validity of the kinematic data may be confirmed by the video data.

Turning to FIG. 7, PBAL 702 is exemplified in operation in an environment within which subject under test (e.g., athlete 704) may wish to be analyzed. It should be noted that athlete 704 is not confined within an indoor laboratory, but is rather being analyzed outdoors where athlete 704 may more naturally progress through her biomechanical movements, which may result in more accurate biomechanical analysis.

In one embodiment, docking stations 710 and 712 may be interconnected to patch panel 716 such that once power (e.g., 5 VDC) is connected to patch panel 716, the respective IMU and EMG sensors connected to docking stations 710 and 712 may also receive power. In this way, the internal batteries of the IMU and EMG sensors may be charged while simultaneously being stored within portable lab 702. In alternate embodiments, docking stations 710 and 712 may additionally provide data interconnectivity so that measurement data stored within the IMU and EMG sensors may be uploaded to laptop 706 (e.g., uploaded from their respective IMU and EMG receiver data log memory as discussed above in relation to FIGS. 4 and 5) all while the IMU and EMG sensors are connected to their respective docking stations 710 and 712.

As illustrated, it can be seen that several sensors 708 have been removed from their respective docking stations 710 and 712 and placed on body segments of athlete 704. Sensors 708 may be enabled with wireless communication capability, such that at least initially, a communication link (e.g., frequency-hopped, DSSS communication link 718) may be established between each sensor 708 and its corresponding receiver (e.g., IMU receiver 212 and EMG receiver 214 as discussed above in relation to FIGS. 2A and 2D). Alternately, or in addition, data logger 720 (e.g., as discussed above in relation to data logger 238 of FIG. 2D) similarly enabled with wireless capability, may be used to record the sensor data as transmitted by sensors 708.

In operation, biomechanical analysis software may be executing on a computing device (e.g., laptop 714), which may be in communication with PBAL 702 (e.g., via the one or more USB connections established between PBAL 702 and laptop 714 via one or more cables 706). The biomechanical analysis software may allow an operator of laptop 714 to synchronize the data collection implemented by each sensor 708 by establishing a "start" signal from laptop 714, which in turn instructs portable lab 702 to generate a synchronization pulse from a pulse generator (e.g., synchronization signal generator 244 of FIG. 2D) within PBAL 702.

An indication of the synchronization pulse may then be transmitted via a communication link (e.g., communication link 718) as may be established between each sensor 708 and its associated receiver (e.g., IMU receiver 212 and EMG receiver 214 as discussed above in relation to FIGS. 2A and 2D). In addition, the synchronization pulse may be provided to patch panel 716 (e.g., via connector 226 of FIG. 2B or connector 266 of FIG. 2C) so that the synchronization pulse may be patched to other equipment (e.g., synchronization input 658 of video capture device 600 of FIG. 6) in the event that video capture device 600 may be utilized during the biomechanical analysis of athlete 704. Accordingly, each video frame captured by video capture device 600 may be synchronized to the data collected by each sensor 708.

Upon receipt of the synchronization pulse, each sensor 708 may begin collecting data and performing various operations on the data collected. For example, the collected data may be processed (e.g., a quaternion may be generated by IMU 206) and then stored within a memory location resident within sensor 708 and/or transmitted to its associated receiver or data logger via communication link 718. Data collection may continue until an operator of laptop 714 terminates the data collection activity.

In one embodiment, athlete 704 may venture beyond the range that may be accommodated by communication link 718 (e.g., 30-50 meters) to the respective receiver contained within PBAL 702 (e.g., receivers 212 and 214 and discussed above in relation to FIGS. 2A and 2D). In such an instance, the data logging function of each sensor 708 may nevertheless continue to store data into its respective data logging memory location (e.g., flash 418 as discussed above in relation to FIG. 4).

Upon completion of the data collection activity, each sensor 708 may be returned to its respective position within its respective docking station (e.g., docking station 710 and 712). In response, the data stored within the data log memory of each sensor 708 may then be uploaded into its respective receiver's memory (e.g., memory 552 as discussed above in relation to FIG. 5), so that any gaps in the received wireless data that may be caused by, for example, an out-of-range sensor 708 may be filled by the wired data upload. Once the integrity of all sensor data is verified, it may then be uploaded to laptop 714 (e.g., via connector 220 of patch panel 216 of FIG. 2B or connector 256 of patch panel 250 of FIG. 2C) via USB cable 706 and analyzed by the biomechanical analysis software executing on laptop 714.

As discussed above, certain applications may require processing of gyroscopic rates that exceed the maximum angular velocity estimates (e.g., 2000 degrees per second) that may be attainable using gyroscopes. In one embodiment, therefore, multiple (e.g., 3) accelerometers arranged in a particular geometric arrangement (e.g., an "L" shape) may be used to implement angular velocity estimates using linear acceleration measurements as may be generated by an IMU (e.g., as discussed above in relation to IMUs 206 of FIGS. 2A and 2D or IMU 416/IMU 368 of FIG. 4).

Figure 8:
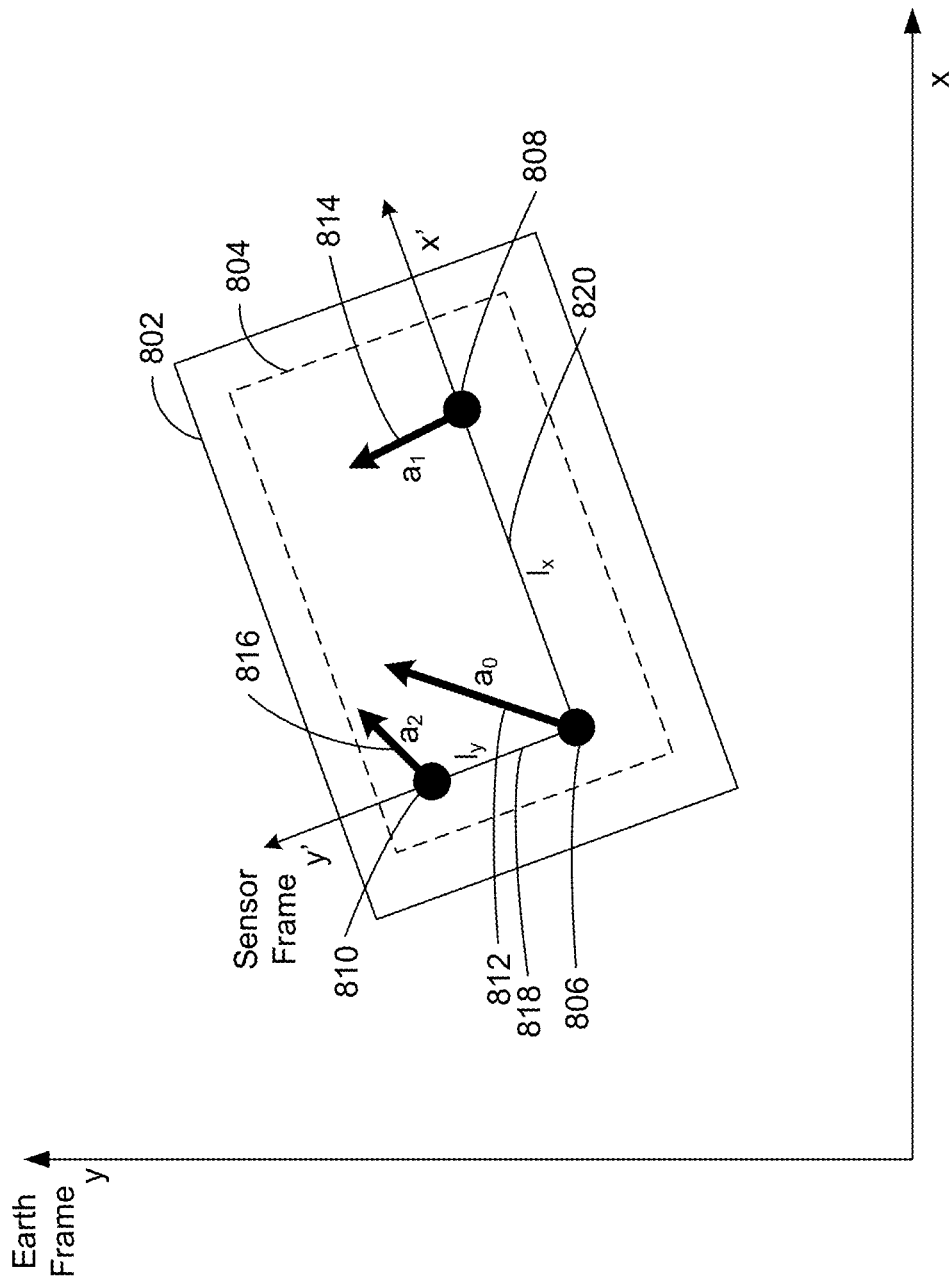
FIG. 8 illustrates a geometric configuration of a triad of linear accelerometers for angular velocity estimation in accordance with one embodiment of the present invention.

FIG. 8 illustrates, for example, three accelerometers (e.g., accelerometers 806, 808 and 810) that may be mounted to printed circuit board (PCB) 804 within sensor module 802. As illustrated, accelerometers 806, 808 and 810 may be mounted in a particular geometric orientation (e.g., an "L" shaped geometric configuration) on PCB 804, where accelerometer 808 may be separated from accelerometer 806 by displacement vector 820 (e.g., the distance $l_x$ along sensor frame axis x' between accelerometer 806 and accelerometer 808) and accelerometer 810 may be separated from accelerometer 806 by displacement vector 818 (e.g., distance $l_y$ along sensor frame axis y' between accelerometer 806 and accelerometer 810).

At any given instant in time: 1) accelerometer 806 may detect linear acceleration (e.g., a linear acceleration that may be described by vector 812, $a_0$); 2) accelerometer 808 may detect linear acceleration (e.g., a linear acceleration that may be described by vector 814, $a_1$); and 3) accelerometer 810 may detect linear acceleration (e.g., a linear acceleration that may be described by vector 816, $a_2$).

The relationship between the linear acceleration vectors at the locations of accelerometers 806 and 808 may be described in equation (1) as:

$$a_1 = a_0 + \alpha \times \Delta r_1 + \omega \times \omega \times \Delta r_1 \quad (1)$$

where x is the cross-product operator, $a_0$ and $a_1$ are the linear acceleration vectors at the locations of accelerometers 806 and 808, respectively; $\omega$ and $\alpha$ are the angular velocity and angular acceleration vectors, respectively, of sensor module 802; and $\Delta r_1$ is the displacement vector 820 having magnitude, $l_x$, along sensor frame axis x'.

Similarly, the linear acceleration vectors at the locations of accelerometers 806 and 810 may be related by equation (2) as:

$$a_2 = a_0 + \alpha \times \Delta r_2 + \omega \times \omega \times \Delta r_2 \quad (2)$$

where $a_2$ is the linear acceleration vector at the location of accelerometer 810 and $\Delta r_2$ is the displacement vector 818 having magnitude, $l_y$, along sensor frame axis y'. By utilizing the linear acceleration vector relationships as described by equations (1) and (2) and by constraining the geometric configuration of accelerometers 806, 808 and 810 (e.g., constrained to the "L" shaped configuration as exemplified in FIG. 8), the angular velocity vector, $\omega$, of sensor module 802 may be determined as described below.

First, expressions for the difference between linear acceleration vectors $a_0$ and $a_1$ and the difference between linear acceleration vectors $a_0$ and $a_2$ may be described as in equations (3) and (4), respectively, as:

$$\Delta a_1 = a_0 - a_1 \quad (3)$$

$$\Delta a_2 = a_0 - a_2 \quad (4)$$

In addition, the "L" shaped configuration constrains displacement vectors $\Delta r_1$ and $\Delta r_2$ as in equations (5) and (6), respectively, as:

$$\Delta r_1 = (l_x \ 0 \ 0) \quad (5)$$

$$\Delta r_2 = (0 \ l_y \ 0) \quad (6)$$

Re-writing equation (1) in terms of equations (3) and (5) in vector format yields:

$$\begin{pmatrix} \Delta a_{1,x} \\ \Delta a_{1,y} \\ \Delta a_{1,z} \end{pmatrix} = \begin{pmatrix} a_x \\ a_y \\ a_z \end{pmatrix} \times \begin{pmatrix} l_x \\ 0 \\ 0 \end{pmatrix} + \begin{pmatrix} \omega_x \\ \omega_y \\ \omega_z \end{pmatrix} \times \begin{pmatrix} \omega_x \\ \omega_y \\ \omega_z \end{pmatrix} \times \begin{pmatrix} l_x \\ 0 \\ 0 \end{pmatrix} \quad (7)$$

while expanding the cross-product terms and simplifying yields equations (8) through (10):

$$\Delta a_{1,x} = -l_x(\omega_y^2 + \omega_z^2) \quad (8)$$

$$\Delta a_{1,x} = -l_x(\omega_x \omega_y + \alpha_z) \quad (9)$$

$$\Delta a_{1,z} = -l_x(\omega_x \omega_z + \alpha_y) \quad (10)$$

Performing the same operations to re-write equation (2) in terms of equations (4) and (6) in vector format, expanding the cross-product terms and simplifying yields equations (11) through (13):

$$\Delta a_{2,x} = l_y(\omega_x \omega_y - \alpha_z) \quad (11)$$

$$\Delta a_{2,y} = -l_y(\omega_x^2 + \omega_z^2) \quad (12)$$

$$\Delta a_{2,z} = l_y(\omega_y \omega_z - \alpha_x) \quad (13)$$

Making the following substitutions:

$$X_1 = \Delta a_{1,x}/l_x \quad (14)$$

$$Y_1 = \Delta a_{1,y}/l_x \quad (15)$$

$$Z_1 = \Delta a_{1,z}/l_x \quad (16)$$

$$X_2 = \Delta a_{2,x}/l_y \quad (17)$$

$$Y_2 = \Delta a_{2,y}/l_y \quad (18)$$

$$Z_2 = \Delta a_{2,z}/l_y \quad (19)$$

$$\Omega_x = \omega_x^2 \quad (20)$$

$$\Omega_y = \omega_y^2 \quad (21)$$

$$\Omega_z = \omega_z^2 \quad (22)$$

yields the following simplified relationships:

$$X_1 = -\Omega_y - \Omega_z \quad (23)$$

$$X_2 = \omega_x \omega_y - \alpha_z \quad (24)$$

$$Y_1 = \omega_x \omega_y + \alpha_z \quad (25)$$

$$Y_2 = -\Omega_x - \Omega_z \quad (26)$$

Adding equation (24) to (25) to cancel $\alpha_z$ yields:

$$Y_1 + X_2 = 2\omega_x \omega_y \quad (27)$$

and squaring the result yields equation (28) in terms of $\Omega_x$ and $\Omega_y$:

$$(Y_1 + X_2)^2 = 4\omega_x^2 \omega_y^2 = 4\Omega_x \Omega_y \quad (28)$$

Subtracting equation (26) from (23) to cancel $\Omega_z$ yields:

$$X_1 - Y_2 = -\Omega_y + \Omega_x \quad (29)$$

and solving for $\Omega_y$ yields equation (30):

$$\Omega_y = Y_2 - X_1 + \Omega_x \quad (30)$$

Substituting equation (30) into equation (28) yields:

$$(Y_1 + X_2)^2 = 4\Omega_x(Y_2 - X_1 + \Omega_x) \quad (31)$$

which may be rearranged into a quadratic equation in terms of $\Omega_x$:

$$4\Omega_x^2 + 4\Omega_x(Y_2 - X_1) - (Y_1 + X_2)^2 = 0 \quad (32)$$

having a real-valued solution expressed as follows:

$$\omega_x^2 = \Omega_x = \frac{1}{2}\left[X_1 + \sqrt{(Y_2 - X_1)^2 + (Y_1 + X_2)^2} - Y_2\right] \quad (33)$$

Solutions for the y and z components may similarly be expressed as in equations (34) and (35), respectively:

$$\omega_y^2 = \Omega_y = \frac{1}{2}\left[-X_1 + \sqrt{(Y_2 - X_1)^2 + (Y_1 + X_2)^2} + Y_2\right] \quad (34)$$

$$\omega_z^2 = \Omega_z = -\frac{1}{2}\left[X_1 + \sqrt{(Y_2 - X_1)^2 + (Y_1 + X_2)^2} + Y_2\right] \quad (35)$$

By taking the square root of equations (33), (34) and (35), the magnitude of each scalar component of the sensor's (e.g., sensor module 802) angular velocity vector may be determined.

In alternate embodiments, accelerometers 806, 808 and 810 may be arranged to form any geometric configuration, where accelerometers 806, 808 and 810 may be placed along orthogonal axes in the sensor frame. As shown in FIG. 8, for example, accelerometers 806, 808 and 810 may be placed along sensor frame axes, x' and y', having displacement vector magnitudes, $l_x$ and $l_y$, respectively, where the intersection of the two displacement vector magnitudes $l_x$ and $l_y$ forms a right angle. In other embodiments (not shown), accelerometers 806, 808 and 810 may be similarly arranged along axes y'/z' having displacement vector magnitudes, $l_y/l_z$, respectively, or along axes z'/x' having displacement vector magnitudes, $l_z/l_x$, respectively. In general, any non-collinear arrangement of accelerometers 806, 808 and 810 may yield similar results, albeit with somewhat more complicated computations being required.

As an example, sensor module 802 may be implemented as a sensor that may be externally connected to a universal sensor pod (e.g., sensor module 368 of FIG. 3C and FIG. 4) whose operation may be sensed by virtue of a sensor code that may be stored within a memory of a connector of sensor module 802 (e.g., EEPROM 372 of sensor module 360 of FIG. 4). In such an instance, a sensor code indicative of the operation of an angular velocity measurement device (e.g., a gyroscope) may be stored within EEPROM 372, such that sensor processor 422 may detect the sensor type of sensor module 802 as that of, for example, a gyroscope irrespective of the fact that other measurement devices (e.g., accelerometers 806, 808 and 810 arranged in an "L" shaped configuration on a PCB within sensor module 802) are instead utilized. In an alternate embodiment, sensor module 802 may exist internally within a universal sensor module (e.g., IMU 416 of sensor pod 300 of FIG. 4) and may perform the angular velocity measurements internal to the universal sensor pod.

In one embodiment, sensor processor 422 may include on-board memory (e.g., flash memory) that may include executable software (e.g., firmware) that may be executed to implement the calculations as described, for example, by equations (1) through (35). In so doing, angular velocity estimates may be generated by sensor processor 422 by manipulating three-dimensional linear acceleration data that may be generated by IMU 416 and/or sensor 368.

Figure 9:
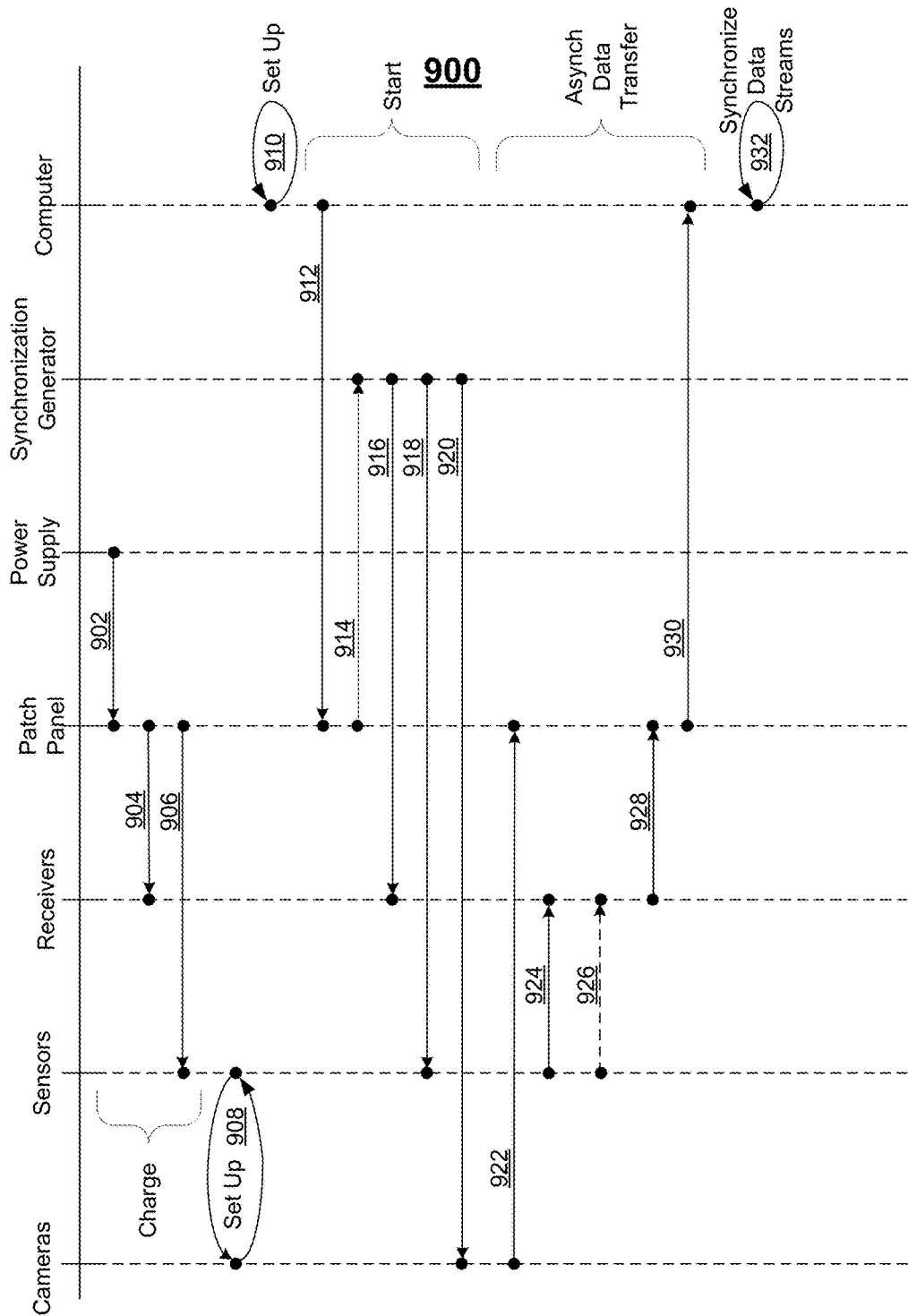
FIG. 9 illustrates a flow diagram of a method of using a portable laboratory in accordance with various embodiments of the present invention.

Turning to FIG. 9, flow diagram 900 is exemplified, in which various data, signal and operational flow diagrams of a PBAL (e.g., PBAL 200 of FIG. 2D) are illustrated. Signal flows 902-906 may represent, for example, a charging cycle, in which signal 902 may represent a power signal (e.g., voltage and current) as provided by a power supply (not shown) to a connector on a patch panel (e.g., connector 222 of patch panel 216 or connector 254 of patch panel 250) as may be implemented, for example, by connecting the power supply to an alternating current (AC) source (e.g., a 110V, 60 Hz power outlet) and connecting the direct current (DC) output from the power supply to the patch panel using an appropriate power cable. In alternate embodiments, the power signal for the charging cycle may be provided by a USB power supply (e.g., a USB power supply from laptop 714 of FIG. 7 via USB cable 706 and patch panel 716). Signal flows 904 and 906 may, for example, represent power signals from the patch panel to the charging inputs of components within the PBAL (e.g., sensors 204, 206 of FIG. 2) so that such components may receive an operational charge into their respective internal batteries adequate for operation for a length of time (e.g., 8 hours). It should be noted, for example, that operational power may be derived from the power supply pin of a USB cable (e.g., USB cable 706 of FIG. 7) so that components (e.g., receivers 212, 214 and synchronization signal generator 244) may receive their operational power from a USB power source (e.g., laptop 714 of FIG. 7).

Operation flow 908 may represent, for example, mobilizing PBAL 200 to a test environment (e.g., a pitching mound, a track and field arena, or a park) through use of mobilization devices (e.g., casters 110 and/or handle 108 of FIG. 1) and preparing PBAL 200 for use as a biomechanical assessment laboratory (e.g., by exposing the biomechanical analysis equipment contained within PBAL 200 as discussed above in relation to FIG. 2A), where the test environment is the environment within which the subject under test most naturally performs his or her biomechanical movements. Once PBAL 200 is prepared for use, the various sensor technologies that may be contained within PBAL 200 may be applied to a subject under test (e.g., subject under test 704 of FIG. 7) and any video capture devices (e.g., cameras 208 of FIG. 2D) may be applied within the test environment as well. Such sensor technologies may include, for example, EMG 204 and IMU 206 technologies, as discussed above in relation to FIG. 2A, and universal sensing technologies, as discussed above in relation to FIGS. 3 and 4, which may further facilitate, for example, acceleration, pressure, and force measurement capabilities. Dynamometers, biosensors (e.g., respiration and electrocardiogram (ECG)), goniometers, generic analog sensors (e.g., +/−10V analog sensors) and generic digital sensors may also be accommodated within PBAL 200.

Operation flow 910 may represent, for example, the preparations required to execute a biomechanical analysis software application that may be hosted on a computing device (e.g., laptop 714 of FIG. 7). Signal flow 912 may, for example, represent a "start" signal that may be transmitted (e.g., transmitted by laptop 714 to patch panel 716 via USB cable 706) by the biomechanical analysis software application to initiate a data gathering session by the sensors and/or cameras as set up in step 908. The "start" signal may then be propagated from the patch panel to a pulse generator (e.g., synchronization signal generator 244 of FIG. 2D) in signal flow 914. In response, the pulse generator may provide substantially simultaneous wireless and/or wired synchronization signals to receivers (e.g., wired synchronization signals 916 to receivers 212 and 214 of FIG. 2D), sensors (e.g., wireless synchronization signals 918 via communication link 718 to sensors 708 of FIG. 7) and cameras (e.g., wired synchronization signals 920 to cameras 208 of FIG. 2D).

Once the sensors and/or cameras have received their respective synchronization signals 916 and 918, asynchronous data streams 922 and 924 may be initiated, where each data stream may contain an embedded synchronization marker to designate that point in time in which the synchronization signal was received relative to the data stream being generated. Data stream 922 may, for example, be transmitted via wired means (e.g., via a USB cable connected from USB connector 656 of FIG. 6B to connectors 232, 234 of patch panel 210 or connectors 268, 270 of patch panel 250). Data stream 924 may, for example, be transmitted by wireless means (e.g., via wireless communication link 718 of FIG. 7).

Optional data stream 926 may, for example, represent a wired data stream (e.g., wired data stream between sensor slots 502/slot multiplexing logic 506 of FIG. 5B to memory 552 of FIG. 5C). Such a wired data stream may be required from sensor data logging memory (e.g., flash memory 418 of FIG. 4) if some or all of data stream 924 was not received properly (e.g., as may be the case if wireless communication link 718 of FIG. 7 became non-functional for one or more periods of time). In such an instance, optional data stream 926 may be used to fill data gaps contained within memory 552 in the case that such data gaps exist as may be determined by processor 554.

Data signal 928 may represent a concatenation of all received sensor data and camera data and may be provided to a patch panel (e.g., connectors 220/236 of patch panels 216/210 or connectors 256/264 of patch panel 250) by one or more sensor receivers (e.g., sensor receiver 550 of FIG. 5C) and video capture devices (e.g., cameras 208 of FIG. 2D) via a network device (e.g., USB hub 242 of FIG. 2D). Data signal 928 may then be patched (e.g., from patch panel 716 as signal 930) over to a computing device (e.g., laptop 714 via one or more USB cables 706).

Once sensor/camera data stream 930 has been received by the computing device (e.g., laptop 714), biomechanical analysis software executing on laptop 714 may parse data stream 930 into separate data streams and may further align each parsed data stream according to the synchronization markers contained within each data stream (e.g., as in operational step 932). In such an instance, each data stream may then become temporally aligned (e.g., aligned in time with respect to the synchronization markers contained within each data stream) to facilitate meaningful and robust biomechanical analyses within laptop 714.

Figure 10:
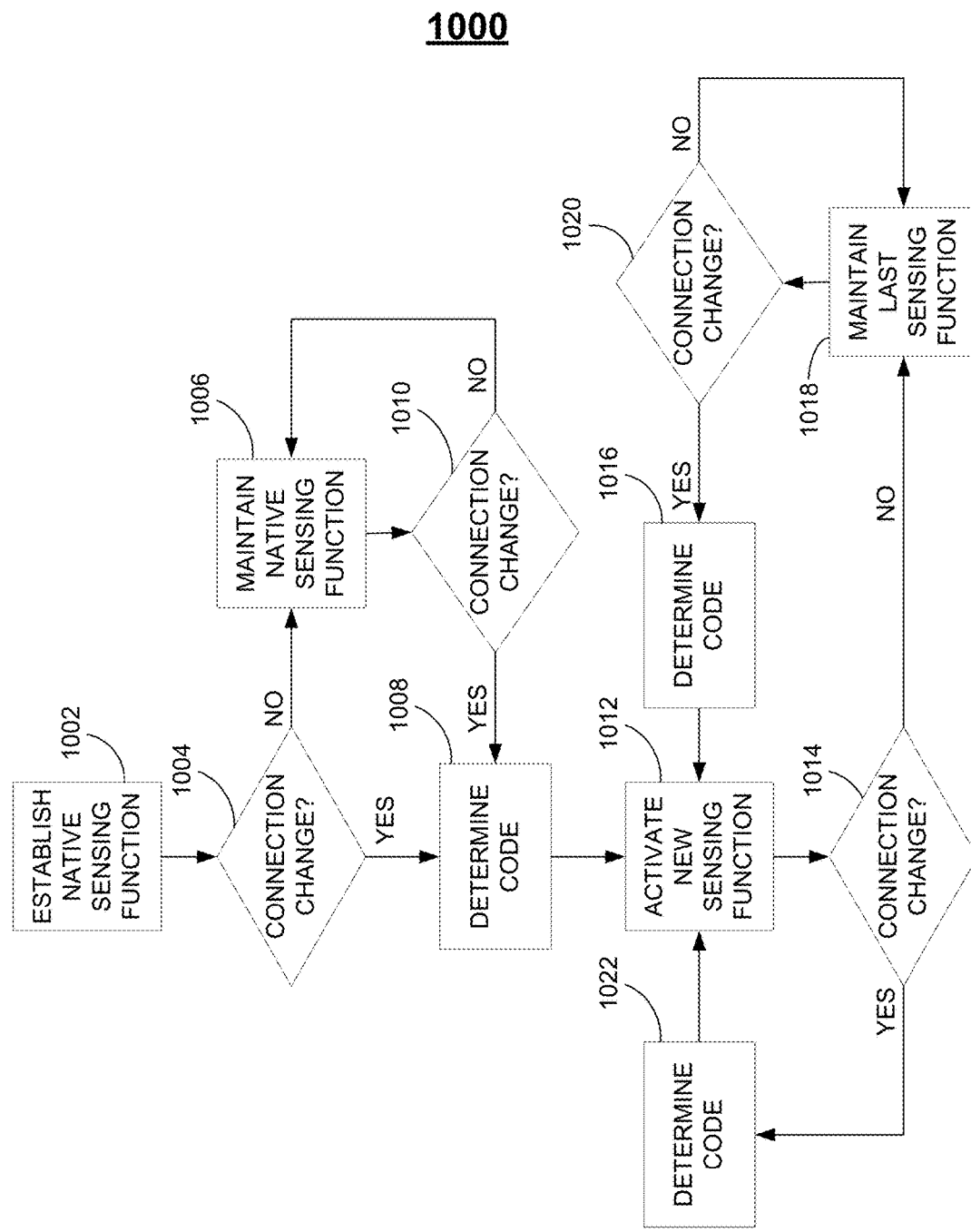
FIG. 10 illustrates a method of using a universal sensor pod in accordance with various embodiments of the present invention.

Turning to FIG. 10, a method of using a universal sensor is exemplified by flow diagram 1000. In step 1002, for example, a universal sensor pod (e.g., sensor pod 300 of FIG. 4) may exhibit native functionality (e.g., IMU and/or EMG functions as provided by IMU 416 and/or sEMG electrodes 352/356 of FIG. 4) with or without a customized sensor (e.g., sensor assembly 360 of FIG. 4) being attached to the universal sensor pod. In such an instance, a native sensing function may be established and made operational in step 1002 (e.g., as discussed above in relation to sensor 708 of FIG. 7).

In step 1004, a determination may be made as to whether a sensor function mode change may be necessary (e.g., by establishing a mechanical and/or electrical connection between a universal sensor (e.g., universal sensor pod 300 of FIG. 4) and a sensor assembly (e.g., sensor assembly 360 of FIG. 4). As an example, a processor (e.g., sensor processor 422 of FIG. 4) may detect a connection (e.g., a connection between connector pair 366/304 and/or 364/306 of FIG. 4) that may be established to provide a communication channel between a universal sensor (e.g., universal sensor pod 300 of FIG. 4) and a sensor assembly (e.g., sensor assembly 360 of FIG. 4). Sensor processor 422 may then receive a code (e.g., retrieve a code contained within EEPROM 372 of FIGS. 3C and 4 as in step 1008) that may be indicative of the sensor function that may be implemented by the sensor assembly (e.g., the sensor function implemented by sensor 368 of FIG. 4).

If the code indicates that a different sensor function is to be initiated (e.g., as in step 1012), then a preconfigured executable application (e.g., a firmware application contained within on-board flash memory 424 of sensor processor 422) may be executed that may be tailored to the particular sensor function being implemented. As a result, sensor data (e.g., sensor data as generated by sensor 368) may be provided either in analog form (e.g., to ADC 420 of FIG. 4 for conversion from analog sensor data to a digital representation of the analog sensor data) or in digital form (e.g., directly to sensor processor 422 from sensor 368) for further processing.

In one embodiment, sensor 368 may, for example, estimate angular velocity by manipulating linear acceleration measurements as discussed above in relation to FIG. 8. In such an instance, sensor 368 (e.g., sensor module 802 of FIG. 8) may either provide angular velocity estimates in digital format (e.g., as may be provided by an onboard processor of sensor module 802) or may instead provide linear acceleration measurements in analog format for further processing (e.g., as discussed above in relation to signal conditioning 402, ADC 420 and sensor processor 422 of FIG. 4) to implement the angular velocity estimate calculations of equations 1 through 35 as discussed above in relation to FIG. 8. Once complete, the manipulated sensor data may then be stored within a memory of the sensor pod.

In steps 1014, 1016, 1018, 1020 and 1022, different functionalities of the universal sensor may be attained simply by exchanging one sensor assembly having one functionality with another sensor assembly having another functionality and detecting that the sensor assembly has been exchanged. For example, if the current universal sensor function is to be changed from a first function (e.g., EMG sensing) to a second function (e.g., pressure sensing), then the sensor change may be detected (e.g., as in steps 1014 or 1020) when a first sensor assembly (e.g., sensor assembly 360 having EMG sensor 368) is disengaged from universal sensor 300 and a second sensor assembly (e.g., sensor assembly 360 having pressure sensor 368). Next, the code associated with the second sensor assembly may be determined (e.g., a code indicative of a pressure sensor may be read by sensor processor 422 from EEPROM 372 of FIG. 4 as in steps 1016 or 1022). In response, the new sensing function may be enabled (e.g., by executing firmware associated with a pressure sensor in sensor processor 422 as in step 1012) and maintained (e.g., as in step 1018) until a different sensor assembly (e.g., sensor assembly 360 of FIG. 4) engages with a universal sensor (e.g., sensor pod 300 of FIG. 4).

Figure 11:
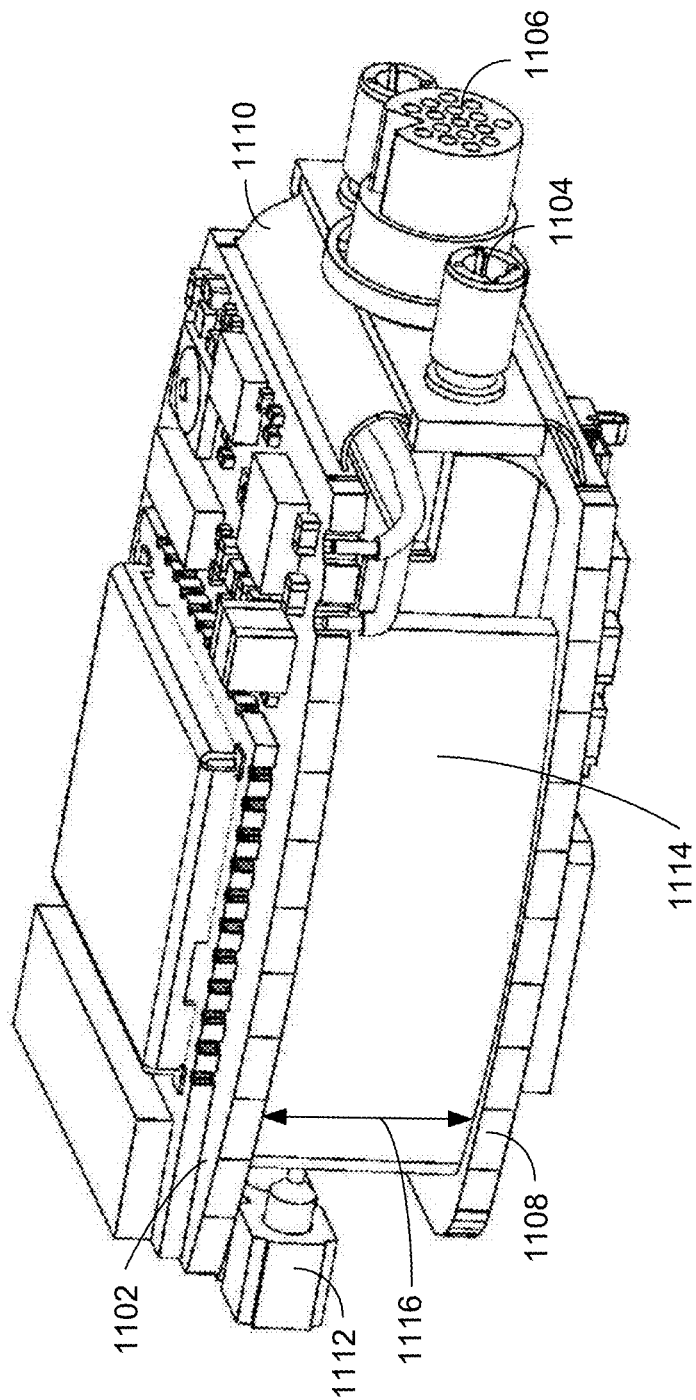
FIG. 11 illustrates an internal hardware configuration of a universal sensor pod in accordance with various embodiments of the present invention.

Turning to FIG. 11, a view of the internal hardware configuration of universal sensor pod 1100 is exemplified, which may correspond to the internal hardware configuration of universal sensor pods 300 as discussed above in relation to FIGS. 3A and 3B. Universal sensor pod 1100 may contain multiple PCBs (e.g., PCBs 1102 and 1108) each of which may contain the components as discussed above in relation to the block diagram of universal sensor pod 300 of FIG. 4 as required.

Data signal and power signal interconnection between PCB 1102, PCB 1108, connectors 1104, 1106 and 1112 may be accomplished, for example, by flexible circuit board 1110, which may accommodate the displacement of PCBs 1102, 1108 around battery compartment 1114. In particular, by establishing separation distance 1116 between PCBs 1102, 1108, a volume of space may be allocated for battery compartment 1114, whereby PCB 1102 marks an upper boundary of the battery compartment volume and PCB 1108 marks a lower boundary of the battery compartment volume.

Other aspects and embodiments of the present invention will be apparent to those skilled in the art from consideration of the specification and practice of the invention disclosed herein. It is intended, therefore, that the specification and illustrated embodiments be considered as examples only, with a true scope and spirit of the invention being indicated by the following claims.

What is claimed is:

1. A universal sensor configured to be worn on a human body segment, the universal sensor comprising:
    a sensor pod including,
        a processor;
        a first memory coupled to the processor and configured with a plurality of executable applications; and
        a second memory; and
    a sensor assembly removably coupled to the sensor pod, the sensor assembly including,
        a first sensor configured to detect a physical property directly associated with the human body segment upon which the universal sensor is worn and further configured to provide a first signal representative of the detected physical property; and
        a third memory configured to provide a code indicative of the detected physical property to the processor, wherein the processor is configured to execute one of the executable applications in response to the code, the executed application causing the processor to manipulate the first signal into a first result and to store the first result in the second memory in response to receiving a synchronization signal; and
    wherein the first result includes a first synchronization marker to designate that point in time in which the sensor pod received the synchronization signal.

2. The universal sensor of claim 1, wherein the sensor pod further includes an analog to digital converter (ADC) coupled to receive the first signal and configured to provide a first digital data stream representative of the first signal, wherein the first digital data stream is stored within the second memory for manipulation by the processor into the first result.

3. The universal sensor of claim 2, wherein the sensor pod further includes a second sensor coupled to the ADC, the second sensor configured to provide a second signal representative of a second sensor function, the ADC being further configured to convert the second signal into a second digital data stream for manipulation by the processor into a second result that is stored within the second memory in response to receiving the synchronization signal, the second result including a second synchronization marker to designate that point in time in which the sensor pod received the synchronization signal.

4. The universal sensor of claim 3, wherein the second sensor function includes electromyography.

5. The universal sensor of claim 4, wherein the second sensor includes,
    first and second electrodes configured to detect muscle activity; and
    a reference electrode configured to reduce noise in the detected muscle activity, wherein the first, second and reference electrodes are arranged on an outer surface of the sensor pod.

6. The universal sensor of claim 3, wherein the sensor pod further includes a third sensor coupled to the ADC, the third sensor configured to provide a third signal representative of a third sensor function, the ADC being further configured to convert the third signal into a third digital data stream for manipulation by the processor into a third result that is stored within the second memory in response to receiving the synchronization signal, the third result including a third synchronization marker to designate that point in time in which the sensor pod received the synchronization signal.

7. The universal sensor of claim 6, wherein the sensor pod further includes a wireless interface coupled to the second memory and configured to wirelessly transmit one or more of the first, second and third results.

* * * * *

UNITED STATES PATENT AND TRADEMARK OFFICE
CERTIFICATE OF CORRECTION

PATENT NO. : 10,058,264 B2
APPLICATION NO. : 15/454580
DATED : August 28, 2018
INVENTOR(S) : Brent R. Perkins and David K. Byman Page 1 of 1

It is certified that error appears in the above-identified patent and that said Letters Patent is hereby corrected as shown below:

On the Title Page

Item (73), 'Noraxton' should read - Noraxon -.

In the Specification

Column 9, Line 52, 'receive' should read - receiver -.

Column 13, equation (3), 'a0-a1' should read - a1-a0 -.

Column 13, equation (4), 'a0-a2' should read - a2-a0 -.

Signed and Sealed this
Second Day of October, 2018

Andrei Iancu
*Director of the United States Patent and Trademark Office*